(12) United States Patent
Terajima et al.

(10) Patent No.: US 7,968,612 B2
(45) Date of Patent: Jun. 28, 2011

(54) MODIFIED ION EXCHANGE RESIN AND PROCESS FOR PRODUCING BISPHENOLS

(75) Inventors: Takashi Terajima, Ichihara (JP); Toshihiro Takai, Ichihara (JP); Hideaki Nakamura, Ota-ku (JP)

(73) Assignee: Mitsui Chemicals, Inc., Tokyo (JP)

( * ) Notice: Subject to any disclaimer, the term of this patent is extended or adjusted under 35 U.S.C. 154(b) by 998 days.

(21) Appl. No.: 11/631,292

(22) PCT Filed: Jun. 14, 2005

(86) PCT No.: PCT/JP2005/011206
§ 371 (c)(1),
(2), (4) Date: Jan. 3, 2007

(87) PCT Pub. No.: WO2006/003803
PCT Pub. Date: Jan. 12, 2006

(65) Prior Publication Data
US 2008/0051480 A1    Feb. 28, 2008

(30) Foreign Application Priority Data

Jul. 2, 2004   (JP) .................................. 2004-196828

(51) Int. Cl.
*C07F 9/54* (2006.01)
(52) U.S. Cl. ............... 521/30; 521/25; 568/11; 568/728
(58) Field of Classification Search ........... 521/30, 521/25; 568/11, 728
See application file for complete search history.

(56) References Cited

U.S. PATENT DOCUMENTS

| | | | |
|---|---|---|---|
| 3,992,432 A * | 11/1976 | Napier et al. | 558/344 |
| 4,303,551 A | 12/1981 | Vaughan | |
| 4,423,252 A | 12/1983 | Maki et al. | |
| 4,478,956 A | 10/1984 | Maki et al. | |
| 5,233,096 A * | 8/1993 | Lundquist | 568/727 |
| 5,395,857 A | 3/1995 | Berg et al. | |
| 5,589,517 A * | 12/1996 | Sugawara et al. | 521/33 |
| 6,281,400 B1 | 8/2001 | Harmer et al. | |
| 6,414,200 B1 | 7/2002 | Spivack et al. | |
| 6,486,364 B2 | 11/2002 | Spivack | |
| 2002/0123534 A1 | 9/2002 | Lundquist | |
| 2002/0123656 A1 | 9/2002 | Spivack | |
| 2004/0127753 A1 | 7/2004 | Iwahara et al. | |
| 2004/0181100 A1 | 9/2004 | Lundquist | |
| 2005/0014910 A1 * | 1/2005 | Lepilleur et al. | 525/524 |
| 2005/0070615 A1 * | 3/2005 | Terajima et al. | 521/25 |

FOREIGN PATENT DOCUMENTS

| | | | |
|---|---|---|---|
| JP | 45-10337 B | | 4/1970 |
| JP | 46-19953 B | | 6/1971 |
| JP | 57-035533 A | | 2/1982 |
| JP | 57-035533 A | * | 2/1982 |
| JP | 62-178532 A | | 8/1987 |
| JP | 04-268316 A | | 9/1992 |
| JP | 05-097741 A | | 4/1993 |
| JP | 06-320009 A | | 11/1994 |
| JP | 08-089819 | * | 4/1996 |
| JP | 08-089819 A | | 4/1996 |
| JP | 08-187436 | * | 7/1996 |
| JP | 08-187436 A | | 7/1996 |
| JP | 10-211433 | * | 8/1998 |
| JP | 10-211433 A | | 8/1998 |
| JP | 10-328573 A | | 12/1998 |
| JP | 2001-122610 A | | 5/2001 |
| JP | 2002-253971 A | | 9/2002 |
| JP | 2003-190805 A | | 7/2003 |
| JP | 2006-340563 A | | 12/2006 |
| WO | WO-00/00045 A1 | | 1/2000 |

OTHER PUBLICATIONS

Office Action in Indian U.S. Appl. No. 11/631,262 mailed Sep. 8, 2010.
Office Action in Indian U.S. Appl. No. 868/DELNP/2007 mailed Sep. 8, 2010.

* cited by examiner

*Primary Examiner* — Peter D. Mulcahy
*Assistant Examiner* — Henry Hu
(74) *Attorney, Agent, or Firm* — Birch, Stewart, Kolasch & Birch, LLP

(57) ABSTRACT

There is provided a modified ion exchange resin catalyst which exhibits higher bisphenols selectivity than the conventional modified ion exchange resins in processes wherein bisphenols are produced by reacting a phenolic compound with ketones, and to provide such a process for producing bisphenols. A modified ion exchange resin is characterized in that at least one compound selected from (A) and (B) shown below is ionically bonded to an acidic functional group of an acidic ion exchange resin:

(A) Compound represented by Formula (1)

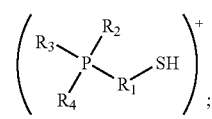

and (B) Compound represented by Formula (2)

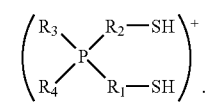

4 Claims, No Drawings

MODIFIED ION EXCHANGE RESIN AND PROCESS FOR PRODUCING BISPHENOLS

TECHNICAL FIELD

The present invention relates to a modified ion exchange resin catalyst and a process for producing bisphenols using the catalyst thereof. More specifically, the invention relates to a modified ion exchange resin catalyst which exhibits a high reaction selectivity, and to a process for producing bisphenols by reacting a phenolic compound with ketones in the presence of the catalyst.

BACKGROUND ART

Bisphenol A [2,2-bis(4-hydroxyphenyl)propane] is usually produced by reacting phenol with acetone in the presence of a homogeneous acid or a solid acid catalyst. The reaction mixture includes unreacted acetone, unreacted phenol, water thus produced, and other by-products, in addition to bisphenol A. The main component of the by-products is 2-(2-hydroxyphenyl)-2-(4-hydroxyphenyl)propane (hereinafter, referred to as o,p'-BPA), and in addition, it includes trisphenol, a polyphenol compound, a chroman compound, minute impurities which can cause coloring, and the like.

Examples of a homogeneous acid to be used as a catalyst, include hydrochloric acid, sulfuric acid, and the like. In the case where the homogeneous acid is used, since it is possible to proceed the reaction while precipitating crystals of an adduct of phenol with bisphenol A by reacting them at lower temperatures, bisphenol A can be produced with a high conversion of acetone and a high selectivity by decreasing the amount of the by-produced o,p'-BPA as an isomer thereof. However, the catalyst of the homogeneous acid such as hydrochloric acid requires a process for removing the catalyst from a reaction mixture or for neutralizing the catalyst, and thus the operation becomes complicated. Homogeneous dissolution of the acid in the reaction solution further causes corrosion of an apparatus or the like. Therefore, expensive and anti-corrosive materials should be used for the reaction apparatus, thus being uneconomical.

As a solid acid catalyst, a sulfonic acid-type cation-exchange resin is usually used. The reaction for producing bisphenol A essentially proceeds only with an acid catalyst, but if such a solid acid catalyst is used, the process in which acetone diffuses from the surface of the catalyst particles to an active site on the catalyst is involved, and thus gives a lower reaction rate than in the homogeneous system. Thus, there is a general method used for improving the catalytic activity and the selectivity by allowing a compound containing a mercapto group to coexist in the reaction system. Specifically, there is a method comprising charging a free-type mercapto group-containing compound such as alkylmercaptan in addition to phenol and acetone which are raw materials to a fixed-bed reactor filled with a sulfonic acid-type cation-exchange resin (for example, Patent Document 1: JP-B No. 45-10337, Patent Document 2: U.S. Pat. No. 6,414,200), and a method comprising covalently bonding a part of sulfonic acid group in a sulfonic acid-type cation-exchange resin with a mercapto group-containing compound or ionically bonding a part of sulfonic acid group in a sulfonic acid-type cation-exchange resin with a mercapto group-containing compound (for example, Patent Document 3: JP-B No. 46-19953). The method of charging a free-type mercapto group-containing compound such as alkylmercaptan in addition to phenol and acetone which are raw materials to a fixed-bed reactor filled with a sulfonic acid-type cation-exchange resin allows specific amount of mercapto group-containing compound to be existed in a reaction system at all times, and thus gives the advantage of less catalyst degradation. However, there is a concern that the mercapto group-containing compound may cause a coloring of bisphenol A, and thus requires a process for removing and recovering the mercapto group-containing compound.

On the other hand, the method of bonding a part of sulfonic acid group in a sulfonic acid-type cation-exchange resin with a mercapto group-containing compound gives a smaller loss of mercapto group-containing compound as compared to the method allowing the free-type mercapto group-containing compound to be existed in a reaction system, and thus is advantageous since there is no need of recovering the mercapto group-containing compound. In particular, there is disclosed in JP-A No. 57-35533 (use of pyridylethanethiol as a mercapto group-containing compound, Patent Document 4), JP-A No. 08-187436 (use of N,N,di-substituted mercaptoalkylamine as a mercapto group-containing compound, Patent Document 5), JP-A No. 08-089819 (use of N,N,N-trimethyl mercaptopropyl ammonium as a mercapto group-containing compound, Patent Document 6), JP-A No. 10-211433 (use of 1,4-dimercaptoalkylpiperidine as a mercapto group-containing compound, Patent Document 7), and U.S. Pat. No. 6,414,200 (use of a silicon-containing alkylmercapto compound as a mercapto group-containing compound, Patent Document 2), that the reaction rate of acetone is increased by improving the structure of a mercapto group-containing compound which to be bonded to a strong-acid ion-exchange resin.

Further, there is also a report related to a sulfonic acid-type cation-exchange resin which is an acid catalyst for improving its activity which is lower than that of the above-described homogeneous acid. When the particle diameter of used sulfonic acid-type cation-exchange resin is large, the reaction materials do not sufficiently diffuse into the particles, thus a sufficient acetone conversion cannot be obtained. Accordingly, it is suggested in JP-A No. 62-178532 (Patent Document 8) to use a sulfonic acid-type cation-exchange resin in a fine particle or a fine powder having an effective diameter of 0.3 mm or less. In JP-A No. 6-340563 (Patent Document 9), the particle diameter of sulfonic acid-type cation-exchange resin to be used and the distribution degree of the particle diameter is likewise provided, and more preferred range is disclosed. Further, in JP-A No. 4-268316 (Patent Document 10) and JP-A No. 2002-253971 (Patent Document 11), methods of forming a sulfonic acid-type cation-exchange resin having a desired particle diameter, are disclosed. As stated, the particle diameter of the sulfonic acid-type cation-exchange resin is an important factor in obtaining a sufficient reaction conversion.

Various improvements on the structure of a resin product, which is the base material of a sulfonic acid-type cation-exchange resin, have been made. The sulfonic acid-type cation-exchange resin is a resin obtained by sulfonating a styrene-divinylbenzene copolymer which is obtained by radically copolymerizing styrene and divinylbenzene. The divinylbenzene in polymerization does not only prevent a polystyrene chain from dissolving in an organic solvent, but the content thereof is also an important factor in controlling the size of a pore (size of a gel micropore) within the sulfonic acid-type cation-exchange resin formed by capturing a polar solvent, or the mechanical strength of the sulfonic acid-type cation-exchange resin. In other words, a sulfonic acid-type cation-exchange resin with a low content of divinylbenzene has a high catalytic activity due to a large gel micropore, but has a low mechanical strength. In addition, if the content thereof is high, the mechanical strength increases, but the gel micropore size decreases, which causes decreased activity.

In order to improve the diffusion within the particles, there are ion-exchange resins in which the degree of crosslinking is increased as the content of divinylbenzene is increased, that are formed with a large hole referred to as a 'macroporous' having a particle diameter of 20 nm or more within the particles by physical treatment. However, in the case where an ion-exchange resin having this macroporous adsorbs a molecule having high polarity, such as water, a crosslinked structure tends to inhibit the bulge of particles caused by the swelling, which eventually collapses when it can no longer endure the swelling. JP-A No. 5-97741 (Patent Document 12) and JP-A No. 6-320009 (Patent Document 13) describe a method which complements the respective defects by simultaneous filling a sulfonic acid-type cation-exchange resin having a low content of divinylbenzene and a sulfonic acid-type cation-exchange resin having a high content of divinylbenzene into a reactor. Further, an improvement on a reaction conversion is reported in Nippon Steel Chemical Co., Ltd. WO 2000/00454 (Patent Document 14), which suggests a sulfonic acid-type cation-exchange resin having large gel micropores by using large molecules such as divinylbiphenyl instead of divinylbenzene.

As such, various techniques related to catalysts have been investigated, particularly for the mercapto group-containing compound, and realized that apart from the ones which are easily available such as aminoethanethiol and pyridineethanethiol, its production process requires many reaction and separation processes, and many of the operations to obtain a product with high purity are complicated. In all cases, there is room for improvement in selectivity. The development of a high selectivity catalyst is demanded. If the improvement in selectivity is attempted, it can not only reduce the load of performing a by-product recovery process in the production process, but it also reduces the material ratio of phenol/acetone without deteriorating the selectivity by increasing the reaction temperature and thus leads to a reduction in cost related to the process for recovering excess phenol. If the activity is reduced in some extent, it can be covered by increasing the size of the reactor, and thus-caused cost-up for producing bisphenol is very small. Therefore, the development of catalyst which is easy to produce and exhibits high selectivity at an equivalent conversion is demanded.

DISCLOSURE OF THE INVENTION

An object of the present invention is to provide a modified ion exchange resin catalyst which exhibits a higher bisphenols selectivity than the conventional modified ion exchange resins in processes for producing bisphenols by reacting a phenolic compound with ketones, and a process for producing bisphenols.

The present inventors have conducted extensive studies to solve the above problems, and as a result, they have found that by using the modified acidic ion exchange resin in which at least one compound selected from the group of compounds represented by the following formulae:

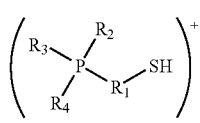 (Formula 1)

(wherein, P is a phosphorous atom; S is a sulfur atom; H is a hydrogen atom; R1 is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and each of R2, R3, and R4 independently is (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, or (3) an aryl group having 5 to 10 carbon atoms, and any one of R2, R3, and R4 may be hydrogen); and

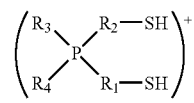 (Formula 2)

(wherein, P is a phosphorous atom; S is a sulfur atom; H is a hydrogen atom; R1 and R2 each is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety may have a phenylene group; and each of R3 and R4 independently is an alkyl group having 1 to 6 carbon atom(s), a cycloalkyl group having 5 to 10 carbon atoms, or an aryl group having 5 to 10 carbon atoms, and any one of them may be hydrogen) is ionically bonded to an acidic functional group of an acidic ion exchange resin, the selectivity of bisphenols is increased, and as a result, bisphenols are obtained with high productivity. Thus, they have completed the invention.

That is, the invention is an acidic ion exchange resin which is partly neutralized by at least one compound selected from the group of compounds represented by the above (Formula 1) and (Formula 2), a catalyst for producing bisphenols formed with this ion exchange resin, and a process for producing bisphenols by using the catalyst.

BEST MODE FOR CARRYING OUT THE INVENTION

The ion exchange resin used for the invention is preferably an acidic ion exchange resin, and examples include common type so called a strong-acid ion-exchange resin which is obtained by introducing a sulfone group into a styrene-divinylbenzene copolymer, and perfluoroalkylsulfonic acid resins such as Nafion.

The modified ion exchange resin of the invention is obtained by ionically bonding an acidic ion exchange resin with at least one compound selected from compounds represented by (Formula 1) and (Formula 2):

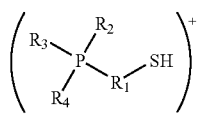 (Formula 1)

(wherein, P is a phosphorous atom; S is a sulfur atom; H is a hydrogen atom; R1 is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and each of R2, R3, and R4 independently is (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, or (3) an aryl group having 5 to 10 carbon atoms, and any one of R2, R3, and R4 may be hydrogen);

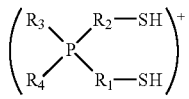

(Formula 2)

(wherein, P is a phosphorous atom; S is a sulfur atom; H is a hydrogen atom; R1 and R2 each is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety may have a phenylene group; and each of R3 and R4 independently is an alkyl group having 1 to 6 carbon atom(s), a cycloalkyl group having 5 to 10 carbon atoms, or an aryl group having 5 to 10 carbon atoms, and any one of them may be hydrogen).

The modified ion exchange resin of the invention either uses the compound selected from compounds represented by (Formula 1) and (Formula 2) alone or in combination of plural kinds. The resin also may be partly neutralized by a cation other than the compound represented by (Formula 1), (Formula 2). Examples of the cation other than the compounds represented by (Formula 1), (Formula 2), include cations of amines and ammoniums, phosphoniums, phosphines, metal cations, and the like.

A preparation of the modified acidic ion exchange resin of the invention is preferably that eventually just before the use in a reaction or during the reaction, at least one cationic compound selected from compounds represented by (Formula 1) and (Formula 2) is ionically bonded to an acidic functional group of an acidic ion exchange resin, and the resin may be prepared by using the cationic compound and/or a precursor forming such state. For example, a neutrally charged compound represented by (Formula 3), (Formula 4) may be contacted as the precursor with an acidic ion exchange resin for cationization.

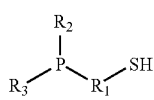

(Formula 3)

(wherein, P is a phosphorous atom; S is a sulfur atom; H is a hydrogen atom; R1 is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and each of R2 and R3 independently is (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, or (3) an aryl group having 5 to 10 carbon atoms)

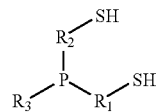

(Formula 4)

(wherein, P is a phosphorous atom; S is a sulfur atom; H is a hydrogen atom; R1 and R2 each is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and R3 is (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, or (3) an aryl group having 5 to 10 carbon atoms)

Examples of the precursor for a mercapto group include thioethers, disulfides, and thioacetates, and these also may be used.

For the compound which is represented by (Formula 1) used for the invention, each of P, S, and H in Formula 1 respectively is a phosphorous atom, a sulfur atom, and a hydrogen atom. R1 is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom, one moiety thereof may have a phenylene group, and the phenylene group may be at the terminal of R1. Each of R2, R3, and R4 independently is any one of (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, and (3) an aryl group having 5 to 10 carbon atoms, and any one of R2, R3, and R4 may be hydrogen.

A compound relatively easy to be synthesized among the compounds represented by (Formula 1) is a compound in which in Formula 1, R1 is an alkylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and one moiety thereof may have a phenylene group; and each of R2, R3, and R4 independently is any one of (1) an alkyl group having 1 to 6 carbon atom(s) which may have a hydroxyl group or an aryl group having 5 to 10 carbon atoms as a substituent and (2) an aryl group having 5 to 10 carbon atoms, and any one of R2, R3, and R4 may be hydrogen.

A more preferable compound among the compounds represented by (Formula 1) is a compound in which in Formula 1, R1 is an alkylene group having 3 to 6 carbon atoms which may have an alkyl group having 1 to 6 carbon atom(s), a cycloalkyl group having 5 to 10 carbon atoms, an aryl group having 5 to 10 carbon atoms, or a hydroxyl group as a substituent, and one moiety thereof may have a phenylene group; and each of R2, R3, and R4 independently is any one of (1) an alkyl group having 1 to 6 carbon atom(s) which may have a hydroxyl group or an aryl group having 5 to 10 carbon atoms as a substituent and (2) an aryl group having 5 to 10 carbon atoms, and any of R2, R3, and R4 may be hydrogen.

Examples of R1 having a phenylene group on its one moiety among those compounds represented by (Formula 1) include —CH2-C6H4-CH2-, —C6H4-CH(CH3)-, —C6H4-CH2-CH2-, and the like, but others may also be included.

For the compound which is represented by (Formula 2) used for the invention, each of P, S, and H in Formula 2 respectively is a phosphorous atom, a sulfur atom, and a hydrogen atom. R1 and R2 each is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; Each of R3 and R4 independently is any one of an alkyl group having 1 to 6 carbon atom(s), a cycloalkyl group having 5 to 10 carbon atoms, and an aryl group having 5 to 10 carbon atoms, and any one of them may be hydrogen.

A compound relatively easy to be synthesized among the compounds represented by (Formula 2) is a compound in which in (Formula 2), R1 and R2 each is an alkylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and one moiety thereof may have a phenylene group; and each of R3 and R4 independently is any one of (1) an alkyl group having 1 to 6 carbon atom(s) which may have a hydroxyl group or an aryl group having 5 to 10 carbon atoms as a substituent and (2) an aryl group having 5 to 10 carbon atoms, and any one of R3 and R4 may be hydrogen.

Examples of R1 and R2 each having a phenylene group on its one moiety among those compounds represented by (Formula 2) include —CH2-C6H4-CH2-, —C6H4-CH(CH3)-, —C6H4-CH2-CH2-, and the like, but others may also be included.

A modification method is not particularly limited. Examples of easy method include contacting in the liquid phase by dissolving in a solution such as water or an organic solvent, and contacting with an ion exchange resin in the gas phase when using a volatile substance.

Examples of the conventionally known method include a method disclosed in JP-B No. 46-19953 and the like. In addition, the compound represented by (Formula 1) can be obtained by reacting a raw material capable of deriving the compound represented by (Formula 1) in the ion exchange resin. Further, a method which eventually forms a modified acidic ion exchange resin may be used such as a method neutralizing an ion exchange resin by using an equivalent or excess amount of cationic compound or precursor thereof, and then partially returning to an acid-type by contacting the ion exchange resin with an acidic solution.

The modified amount of modified acidic ion exchange resin catalyst in the invention is preferably 0.1 to 50% of total sulfonic acid group. Thereby, it is possible to exhibit the modification effect to a maximum extent without causing the decrease in the activity due to the decrease in an amount of acid.

The method of measuring the amount of acid of the ion exchange resin is not particularly limited, but can be determined by a general method of measuring the exchange content of an acidic ion exchange resin. In the invention, the amount is determined from a titration curve obtained by stirring 0.2 g of a dry resin in 200 ml of a 10% aqueous NaCl solution for one hour and titrating the whole amount of the filtrate with a 0.05 N aqueous NaOH solution.

In the invention, for phenol to be used as a raw material for producing bisphenol A, a generally available industrial phenol can be used. The industrial phenol includes one prepared by a cumene method, a toluene oxidation method, or the like, and any of which may be used. Generally, phenol having a purity of 98% or more is commercially available. Such the industrial phenol may be used as it is in the synthesis reaction of bisphenol A, but preferably phenol which is preliminarily treated with a strong acid-type cation-exchange resin in a continuous or batch mode before carrying out the reaction at a treatment temperature of 50 to 120° C. during a contact time of 5 minutes to 10 hours and polymerized with a carbonyl compound derived from acetone, is used. Even more preferably, one obtained by the process wherein the industrial phenol is brought into contact with a strong acid-type cation-exchange resin as described above and is then subjected to a distillation treatment under the condition of a normal pressure to a reduced pressure of 10 mmHg, at a temperature of 70 to 200° C., is used.

Acetone used in the invention is not particularly limited, but it may be a commercially available industrial acetone. Generally, acetone having a purity of 99% or more is available.

The amounts (quantitative ratios) of phenol and acetone, used as raw materials, to be used, are not particularly limited, but the molar ratio of phenol/acetone is recommended to be preferably in the range of 0.1 to 100, and more preferably in the range of 0.5 to 50. If the amount of phenol is too small, it is difficult to accomplish a high conversion of acetone as a raw material, if the amount of phenol is too large, the reactor becomes unreasonably larger because phenol is used as the higher amount than required, and moreover, massive circulation of phenol is also required, even though a high conversion of acetone can be accomplished. Thus, efficient production cannot be accomplished.

As disclosed in EP No. 583712, the mixture of those raw materials may preliminarily contain 1 or less % of water.

In the invention, the reaction temperature is not particularly limited, but it is preferably in the range of 0 to 300° C., and more preferably in the range of 30 to 200° C. If the reaction temperature is extremely low, the reaction rate decreases and thus the productivity of a reaction product also decreases. On the other hand, if the reaction temperature is extremely high, an undesirable side reaction, or the like proceeds, thus leading to the increase in the amount of by-products. The excessively high reaction temperature is unfavorable for stability of phenol and acetone as raw materials and further bisphenol A as a product, decreases the reaction selectivity, and is not economical. Therefore, it is not economical.

The reaction can be carried out under any of a reduced pressure, an applied pressure, and a normal pressure. From the viewpoint of the reaction efficiency (reaction efficiency per unit volume), it is not preferable to carry out the reaction under too low of pressure. Usually, the pressure for carrying out the reaction is preferably in the range of 0.01 to 20 MPa, and more preferably in the range of 0.05 to 10 MPa. Of course, the invention is not limited to such pressure ranges.

In addition, when carrying out the invention, the amount of the catalyst to be used is not particularly limited, but for example, when carrying out the reaction in a batch mode, it is recommended to carry out the invention preferably in the range of 0.001 to 200% by weight, and more preferably in the range of 0.1 to 50% by weight with respect to phenol as a raw material.

When carrying out the invention, it is possible to carry out the reaction in the diluted state by adding a solvent or gas which is inert to the catalyst and the reaction reagent in the reaction system. Specifically, aliphatic hydrocarbons such as methane, ethane, propane, butane, hexane, and cyclohexane, and an inert gas such as nitrogen, argon, and helium, and if necessary, hydrogen can be used as diluents.

When carrying out the invention, the method can be carried out in any of a batch, semi-batch, or continuous flow system. It can be carried out in any of a liquid phase, a gas phase, and a gas-liquid mixed phase. Preferably, from the viewpoint of the reaction efficiency, it is recommended that the reaction is carried out in the liquid phase. For a method for charging a catalyst, various kinds of methods using, for example, a fixed bed, a fluidized bed, a suspended bed, and a plate fixed bed can be employed, and any of which can be used.

The reaction time (retention time or catalytic contact time in the flow system) is not particularly limited, but it is usually 0.1 second to 30 hours, and preferably 0.5 second to 15 hours. After the reaction, the reaction product can be separated and recovered from the catalysts, or the like, by a separation method such as filtration, extraction, and distilling-off. Bisphenol A as a desired product can be separated, purified from the recovered compound by performing a sequential treatment of solvent extraction, distillation, alkali treatment, acid treatment and the like or an ordinary separation and purification method suitably combining them, and obtained. In addition, unreacted raw materials can be recovered and recycled into the reaction system for use.

In the case of a batch reaction, the catalyst which is separated and recovered from the reaction product after the reaction, can be used as it is, or partially or wholly reproduced to be repeatedly used for the reaction. In the case of carrying out the reaction in a fixed bed or a fluidized bed flow reaction system, if the catalyst is provided to the reaction and thereby a part or all of the catalysts is inactivated or is lowered in the activity, the reaction is interrupted, and thereafter the catalyst can be reproduced and then provided to the reaction. Alternatively, a part of the catalyst can be withdrawn continuously or intermittently and reproduced, and then recycled to the reactor for re-use. Further, a fresh catalyst can be intermittently supplied to the reactor. When carrying out the reaction in a moving-bed flow reaction, the catalyst can be separated, recovered and, if necessary, reproduced, as in the batch reaction.

A catalyst can be reproduced by using any method as long as its catalytic ability is recovered, and for example the catalyst may be washed with water or an organic solvent, or may be subjected to a re-modification after being washed with an acidic solvent. In addition, the catalyst may be modified after being washed alternately with an acidic solvent and a basic solvent several times and finally with an acidic solvent.

EXAMPLES

Hereinafter, the present invention will be described in more detail with reference to Examples. However, the invention is not intended to be limited to Examples.

Herein, although an ion exchange resin of same brand is used, since there may be a case where its catalytic ability differs in a BPA synthesis reaction as its lot differs, Amberlyst 31 of same brand and same lot is used in all Examples and Comparative Examples below.

Example 1

(1) Synthesis of (3-mercaptopropyl)triphenylphosphoniumbromide 14.0 g of (3-mercaptopropyl)triphenylphosphoniumbromide and 2.35 g of thiourea were dissolved in 335 ml of ethanol, and the mixture was refluxed for about 16 hours. The resultant solution was ice-cooled, filtered, and thus-obtained solid was sufficiently dried to obtain White Crystal 1. 5.3 g of White Crystal 1 was dissolved in 100 ml of thoroughly deaerated ion-exchange water, and thereto an aqueous solution prepared by dissolving 0.5 g of sodium hydroxide to 25 ml of ion-exchange water was added dropwise for 30 minutes under a nitrogen atmosphere. Thereafter, the mixture was stirred at 60° C. for 2 hours and cooled, under a nitrogen atmosphere. The solid obtained by filtration was washed with ion-exchange water, further dissolved in chloroform, and repeatedly, subjected washing with ion-exchange water and a separation. The chloroform phase was desolvated, and thus obtained solid was recrystallized from chloroform and dried to obtain White Crystal 2. When White Crystal 2 was analyzed with $^1$H-NMR and FD-MS measurements, it was confirmed to have a structure of Formula 5.

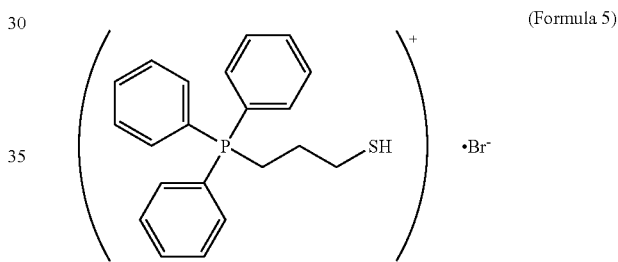

(Formula 5)

(2) Preparation of (3-mercaptopropyl)triphenylphosphonium modified ion exchange resin catalyst 3 g of thoroughly washed and dried Amberlyst 31 was stirred vigorously in 60 ml of 50% aqueous acetonitrile solution. Thereto, 30 ml of 0.077 mol/L (3-mercaptopropyl)triphenylphosphoniumbromide-50% aqueous acetonitrile solution which is prepared by using White Crystal 2 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. at least 10 hours to obtain Catalyst 1. The amount of acid of the catalyst in a dry-state was 3.47 milliequivalents/g.

(3) Bisphenol A Synthesis Reaction

To a 70 ml pressure-resistant reactor, 0.35 g of Catalyst 1 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 88.1% and the selectivity of pp'-bisphenol A was 94.1%.

Example 2

(1) Synthesis of (4-mercaptobutyl)triphenylphosphoniumbromide 11.0 g of (4-bromobutyl)triphenylphosphoniumbromide and 1.75 g of thiourea were dissolved in 250 ml of ethanol, and the mixture was refluxed for about 16 hours. About 170 ml of ethanol was distilled-off therefrom, further the reaction solution was cooled to not more than 0° C., and then left over for a filtration. Thus-obtained solid was sufficiently washed with chloroform and dried to obtain White Crystal 3. 6.0 g of White Crystal 3 was dissolved in 140 ml of thoroughly deaerated ion-exchange water, and thereto 30 ml of 1.6% aqueous sodium hydroxide solution was added dropwise under a nitrogen atmosphere. Thereafter, the mixture was stirred under a nitrogen atmosphere at 60° C. for 2 hours, and cooled. Thereto, a 12 ml of 5.6% aqueous HBr solution was added. Thereto, 70 ml of chloroform was added, well mixed, and then the water phase and chloroform phase were separated. The chloroform phase was desolvated to obtain White Crystal 4. When White Crystal 4 was analyzed with $^1$H-NMR and LC-MS measurements, it was confirmed to have a structure of Formula 6.

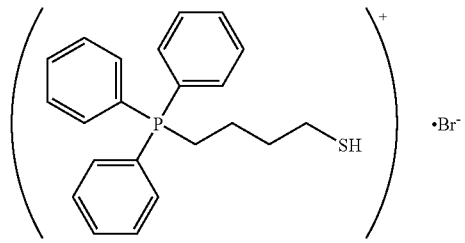

(Formula 6)

(2) Preparation of (4-mercaptobutyl)triphenylphosphonium modified ion exchange resin catalyst 3 g of thoroughly washed and dried Amberlyst 31 was stirred vigorously in 60 ml of ion-exchange water. Thereto, 196 ml of 0.0116 mol/L (4-mercaptobutyl)triphenylphosphoniumbromide-aqueous solution which is prepared by using White Crystal 4 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 2. The amount of acid of the catalyst in a dry-state was 3.49 milliequivalents/g.

(3) Bisphenol A Synthesis Reaction

To a 70 ml pressure-resistant reactor, 0.35 g of Catalyst 2 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 94.9% and the selectivity of pp'-bisphenol A was 93.9%.

Example 3

(1) Synthesis of (5-mercaptopentyl)triphenylphosphoniumbromide 20.7 g of 1,5-dibromopentane and 23.6 g of triphenylphosphin were dissolved in 55 ml of toluene, and the mixture was stirred at about 60° C. for 18 hours. Thereafter, supernatant toluene was removed, the residual was dissolved in ion-exchange water, and the resultant aqueous solution was repeatedly extruded using toluene. Next, the aqueous solution was mixed by adding chloroform, separated, and obtained chloroform phase was repeatedly extruded by using ion-exchange water and the chloroform phase was desolvated, to obtain White Crystal 5. 7.0 g of White Crystal 5 and 1.1 g of thiourea were dissolved in 150 ml of ethanol, and the mixture was refluxed for about 16 hours. Ethanol was distilled-off from the solution, and then dried to obtain White Crystal 6. 3.0 g of White Crystal 6 was dissolved in 75 ml of thoroughly deaerated ion-exchange water, and thereto 17 ml of 1.6% aqueous sodium hydroxide solution was added dropwise under a nitrogen atmosphere. Thereafter, the mixture was stirred under a nitrogen atmosphere at 60° C. for 2 hours, and cooled. Thereto, a 8 ml of 5.6% aqueous HBr solution was added. Thereto, 30 ml of chloroform was added, well mixed, and then the water phase and chloroform phase were separated. The chloroform phase was desolvated to obtain White Crystal 7. When White Crystal 7 was analyzed with $^1$H-NMR and LC-MS measurements, it was confirmed to have a structure of Formula 7.

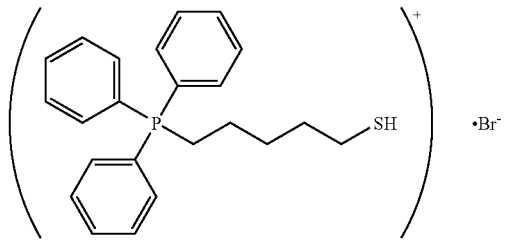

(Formula 7)

(2) Preparation of (5-mercaptopentyl)triphenylphosphonium modified ion exchange resin catalyst 3 g of thoroughly washed and dried Amberlyst 31 was stirred vigorously in 60 ml of ion-exchange water. Thereto, 55 ml of 0.042 mol/L (5-mercaptopentyl)triphenylphosphoniumbromide-aqueous solution which is prepared by using White Crystal 7 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. at least 10 hours to obtain Catalyst 3. The amount of acid of the catalyst in a dry-state was 3.43 milliequivalents/g.

(3) Bisphenol A Synthesis Reaction

To a 70 ml pressure-resistant reactor, 0.35 g of Catalyst 3 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 94.9% and the selectivity of pp'-bisphenol A was 94.0%.

Example 4

(1) Synthesis of (6-mercaptohexyl)triphenylphosphoniumbromide 23.4 g of 1,6-dibromohexane and 25.0 g of triphenylphosphin were dissolved in 35 ml of toluene, and the mixture was stirred at about 60° C. for 18 hours. Thereafter, supernatant toluene was removed, the residual was dissolved in ion-exchange water, and the resultant aqueous solution was repeatedly extruded using toluene. Next, the aqueous solution was mixed by adding chloroform, separated, and obtained chloroform phase was repeatedly extruded by using ion-exchange water and the chloroform phase was desolvated, to obtain White Crystal 8. 7.2 g of White Crystal 8 and 1.1 g of thiourea were dissolved in 150 ml of ethanol, and the mixture was refluxed for about 16 hours. Ethanol was distilled-off from the solution, and then dried to obtain White Crystal 9. 3.1 g of White Crystal 9 was dissolved in 75 ml of thoroughly deaerated ion-exchange water, and thereto 17 ml of 1.6% aqueous sodium hydroxide solution was added dropwise under a nitrogen atmosphere. Thereafter, the mixture was stirred under a nitrogen atmosphere at 60° C. for 2 hours, and cooled. Thereto, a 8 ml of 5.6% aqueous HBr solution was added. Thereto, 30 ml of chloroform was added, well mixed, and then the water phase and chloroform phase were separated. The chloroform phase was desolvated to obtain White Crystal 10. When White Crystal 10 was analyzed with $^1$H-NMR and LC-MS measurements, it was confirmed to have a structure of Formula 8.

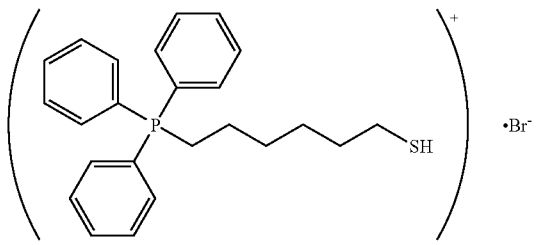

(Formula 8)

(2) Preparation of (6-mercaptohexyl)triphenylphosphonium modified ion exchange resin catalyst 3 g of thoroughly washed and dried Amberlyst 31 was stirred vigorously in 60 ml of ion-exchange water. Thereto, 55 ml of 0.042 mol/L (6-mercaptohexyl)triphenylphosphonium-bromide-aqueous solution which is prepared by using White Crystal 10 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 4. The amount of acid of the catalyst in a dry-state was 3.41 milliequivalents/g.

(3) Bisphenol A Synthesis Reaction

To a 70 ml pressure-resistant reactor, 0.35 g of Catalyst 4 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 95.1% and the selectivity of pp'-bisphenol A was 94.1%.

Example 5

(1) Synthesis of (4-mercaptobutyl)diphenyl(p-tolyl)phosphoniumbromide 15.3 g of 1,4-dibromobutane and 19.2 g of diphenyl(p-tolyl)phosphin were dissolved in 40 ml of toluene, and the mixture was stirred under a nitrogen atmosphere at about 70° C. for 16 hours. The resultant solution was cooled, filtered, and thus-obtained solid was washed with toluene and dried to obtain White Crystal 11. 10 g of White Crystal 11 and 1.55 g of thiourea were dissolved in 250 ml of ethanol, and the mixture was refluxed for about 16 hours. Ethanol was distilled-off from the solution, and thus-obtained solid washed with ethanol and dried to obtain White Crystal 12. 6.0 g of White Crystal 12 was dissolved in 140 ml of thoroughly deaerated ion-exchange water, and thereto 31 ml of 1.6% aqueous sodium hydroxide solution was added dropwise under a nitrogen atmosphere. Thereafter, the mixture was stirred under a nitrogen atmosphere at 60° C. for 2 hours, and cooled. Thereto, a 13 ml of 5.6% aqueous HBr solution was added. Thereto, 70 ml of chloroform was added, well mixed, and then the water phase and chloroform phase were separated. The chloroform phase was desolvated to obtain White Crystal 13. When White Crystal 13 was analyzed with $^1$H-NMR and LC-MS measurements, it was confirmed to have a structure of Formula 9.

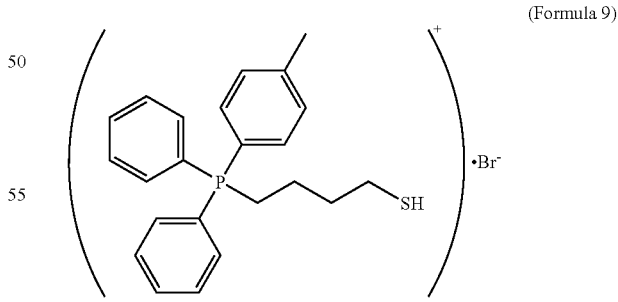

(Formula 9)

(2) Preparation of (4-mercaptobutyl)diphenyl(p-tolyl)phosphonium modified ion exchange resin catalyst 3 g of thoroughly washed and dried Amberlyst 31 was stirred vigorously in 60 ml of ion-exchange water. Thereto, 196 ml of 0.0116 mol/L (4-mercaptobutyl)diphenyl(p-tolyl)phosphoniumbromide-aqueous solution which is prepared by using White Crystal 13 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 5. The amount of acid of the catalyst in a dry-state was 3.43 milliequivalents/g.

(3) Bisphenol A Synthesis Reaction

To a 70 ml pressure-resistant reactor, 0.35 g of Catalyst 5 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 93.3% and the selectivity of pp'-bisphenol A was 93.8%.

Example 6

(1) Synthesis of (4-mercaptomethylbenzyl)triphenylphosphoniumbromide 6.3 g of 1,4-bis(bromomethyl)benzene and 6.5 g of triphenylphosphin were dissolved in 60 ml of toluene, and the mixture was stirred under a nitrogen atmosphere at about 60° C. for 3 hours. The resultant solution was cooled, filtered, and thus-obtained solid was washed with toluene and dried to obtain White Crystal 14. 10 g of White Crystal 14 and 1.5 g of thiourea were dissolved in 100 ml of ethanol, and the mixture was refluxed for about 2 hours. Ethanol was distilled-off from the solution, and thus-obtained solid was dried to obtain White Crystal 15. 11.0 g of White Crystal 15 was dissolved in 300 ml of thoroughly deaerated ion-exchange water, and thereto 15 ml of 5.4% aqueous sodium hydroxide solution was added dropwise under a nitrogen atmosphere. Thereafter, the mixture was stirred under a nitrogen atmosphere at 60° C. for 3 hours, and cooled. Thereto, a 7.8 ml of 5.3% aqueous HBr solution was added. After being stirred for several minutes, the mixture was left to settle, the water phase was taken out and cooled, and left as it is for another 16 hours to settle. The resultant was filtered, and thus-obtained solid was washed with cold water and dried to obtain White Crystal 16. When White Crystal 16 was analyzed with $^1$H-NMR and LC-MS measurements, it was confirmed to have a structure of Formula 10.

(Formula 10)

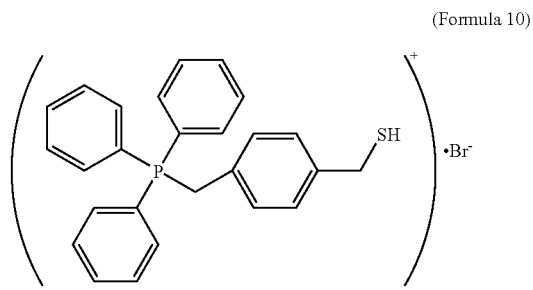

(2) Preparation of (4-mercaptomethylbenzyl)triphenylphosphonium modified ion exchange resin catalyst 3 g of thoroughly washed and dried Amberlyst 31 was stirred vigorously in 60 ml of 25% aqueous acetonitrile solution. Thereto, 120 ml of 0.0188 mol/L (4-mercaptomethylbenzyl)triphenylphosphoniumbromide-25% aqueous acetonitrile solution which is prepared by using White Crystal 16 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 6. The amount of acid of the catalyst in a dry-state was 3.40 milliequivalents/g.

(3) Bisphenol A Synthesis Reaction

To a 70 ml pressure-resistant reactor, 0.35 g of Catalyst 6 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 93.9% and the selectivity of pp'-bisphenol A was 94.0%.

Example 7

(1) Synthesis of (4-mercaptomethylbenzyl)diphenylpropylphosphoniumbromide 6.3 g of 1,4-bis(bromomethyl)benzene and 5.4 g of diphenylpropylphosphin were dissolved in 60 ml of toluene, and the mixture was stirred under a nitrogen atmosphere at about 60° C. for 5 hours. The resultant solution was cooled, filtered, and thus-obtained solid was washed with toluene and dried to obtain White Crystal 17. 10 g of White Crystal 17 and 1.53 g of thiourea were dissolved in 100 ml of ethanol, and the mixture was refluxed for about 3 hours. Ethanol was distilled-off from the solution, and thus-obtained solid was dried to obtain White Crystal 18. 11.0 g of White Crystal 18 was dissolved in 300 ml of thoroughly deaerated ion-exchange water, and thereto 15 ml of 5.4% aqueous sodium hydroxide solution was added dropwise under a nitrogen atmosphere. Thereafter, the mixture was stirred under a nitrogen atmosphere at 60° C. for 3 hours, and cooled. Thereto, a 7.8 ml of 5.3% aqueous HBr solution was added. After being stirred for several minutes, the mixture was left to settle, the water phase was taken out and cooled, and left as it is for another 16 hours to settle. The resultant was filtered, and thus-obtained solid was washed with cold water and dried to obtain White Crystal 19. When White Crystal 19 was analyzed with $^1$H-NMR and LC-MS measurements, it was confirmed to have a structure of Formula 11.

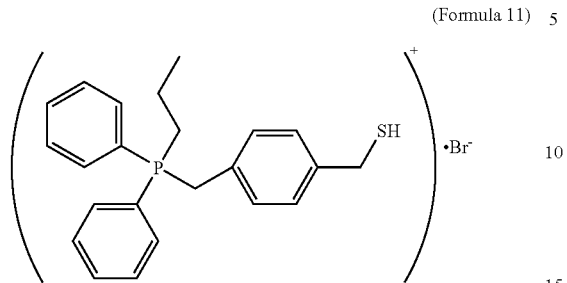

(Formula 11)

(2) Preparation of (4-mercaptomethylbenzyl)diphenylpropylphosphonium modified ion exchange resin catalyst 3 g of thoroughly washed and dried Amberlyst 31 was stirred vigorously in 60 ml of 25% aqueous acetonitrile solution. Thereto, 120 ml of 0.0188 mol/L (4-mercaptomethylbenzyl)triphenylphosphoniumbromide-25% aqueous acetonitrile solution which is prepared by using White Crystal 19 obtained from (1) was slowly added dropwise. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 7. The amount of acid of the catalyst in a dry-state was 3.43 milliequivalents/g.

(3) Bisphenol A Synthesis Reaction

To a 70 ml pressure-resistant reactor, 0.35 g of Catalyst 7 prepared in (2), 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 94.8% and the selectivity of pp'-bisphenol A was 94.1%.

Comparative Example 1

While stirring 3 g of thoroughly washed and dried Amberlyst 31 in 60 ml of ion-exchange water, 30 ml of 0.077 mol/L aminoethanethiol hydrochloride aqueous solution was slowly added dropwise thereto. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 2. The amount of acid of the catalyst in a dry-state was 4.14 milliequivalents/g.

To a 70 ml pressure-resistant reactor, 0.35 g of Catalyst 2, 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 84.9% and the selectivity of pp'-bisphenol A was 91.5%.

Comparative Example 2

While stirring 3 g of thoroughly washed and dried Amberlyst 31 in 60 ml of ion-exchange water, 30 ml of 0.077 mol/L 4-pyridineethanethiol hydrochloride aqueous solution was slowly added dropwise thereto. After the dropwise addition, the mixture was subsequently stirred for 5 hours, and then repeatedly subjected to a filtration and washing with ion-exchange water. Thereafter, the resultant was vacuum dried at 80° C. for at least 10 hours to obtain Catalyst 3. The amount of acid of the catalyst in a dry-state was 3.94 milliequivalents/g.

To a 70 ml pressure-resistant reactor, 0.35 g of Catalyst 3, 6.63 g of phenol, and 0.37 g of acetone were charged, and the reactor was pressurized with nitrogen gas under 0.5 MPa of a gauge pressure, and then the reaction was conducted with heating and stirring at 75° C. for 2 hours. Thereafter, the resultant was cooled to room temperature. After the pressure discharge, the reaction solution was taken out, and analytically quantified by a liquid chromatography method. As a result, the conversion of acetone was 94.0% and the selectivity of pp'-bisphenol A was 91.6%.

INDUSTRIAL APPLICABILITY

According to the present invention, it is possible to produce bisphenols with good yield and selectivity, and to produce bisphenols with remarkably excellent safety, process, and cost.

The invention claimed is:

1. A modified ion exchange resin, wherein at least one cation selected from (A) and (B) shown below is ionically bonded to an acidic functional group of an acidic ion exchange resin, (A) a cation represented by Formula 1:

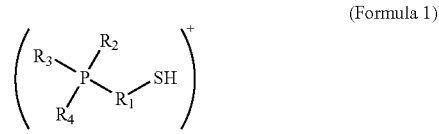

(Formula 1)

wherein, P is a phosphorous atom; S is a sulfur atom; H is a hydrogen atom; $R_1$ is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and each of $R_2$, $R_3$, and $R_4$ independently is (1) an alkyl or an alkenyl group having 1 to 6 carbon atom(s) which may have a hydroxyl group or an aryl group having 5 to 10 carbon atoms as a substituent, (2) a cycloalkyl group having 5 to 10 carbon atoms, or (3) an aryl group having 5 to 10 carbon atoms, and any one of $R_2$, $R_3$, and $R_4$ may be hydrogen; and (B) a cation represented by Formula 2:

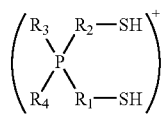
(Formula 2)

wherein, P is a phosphorous atom; S is a sulfur atom; H is a hydrogen atom; $R_1$ and $R_2$ each is an alkylene or an alkenylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and in which the one carbon may be replaced to a silicon atom and one moiety thereof may have a phenylene group; and each of $R_3$ and $R_4$ independently is an alkyl group having 1 to 6 carbon atom(s), a cycloalkyl group having 5 to 10 carbon atoms, or an aryl group having 5 to 10 carbon atoms, and any one of them may be hydrogen, wherein said cation is ionically bonded to 0.1 to 50 mol % of the total acidic functional groups existing in said acidic ion exchange resin.

2. The modified ion exchange resin according to claim 1, wherein in the cation represented by the above Formula 1, $R_1$ is an alkylene group having 1 to 6 carbon atom(s) which may have an alkyl group having 1 to 6 carbon atom(s), a cycloalkyl group having 5 to 10 carbon atoms, an aryl group having 5 to 10 carbon atoms, or a hydroxyl group as a substituent, and one moiety thereof may have a phenylene group; and each of $R_2$, $R_3$, and $R_4$ independently is (1) an alkyl group having 1 to 6 carbon atom(s) which may have a hydroxyl group or an aryl group having 5 to 10 carbon atoms as a substituent or (2) an aryl group having 5 to 10 carbon atoms, and any one of $R_2$, $R_3$, and $R_4$ may be hydrogen.

3. The modified acidic ion exchange resin according to claim 1, wherein the cation represented by the above Formula 1 is at least one compound represented by the following Formula 3:

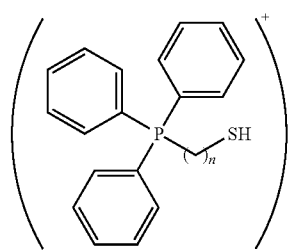
(Formula 3)

wherein, P is a phosphorous atom; S is a sulfur atom; H is a hydrogen atom; and n is an integer of 1 to 4.

4. The modified acidic ion exchange resin according to claim 1, wherein the acidic ion exchange resin is obtained by introducing a sulfonyl group into a styrene polymer and/or a styrene-divinylbenzene copolymer.

\* \* \* \* \*